March 12, 1940. J. S. ELLIOTT Plant Pat. 370
ROSE PLANT
Filed July 11, 1939
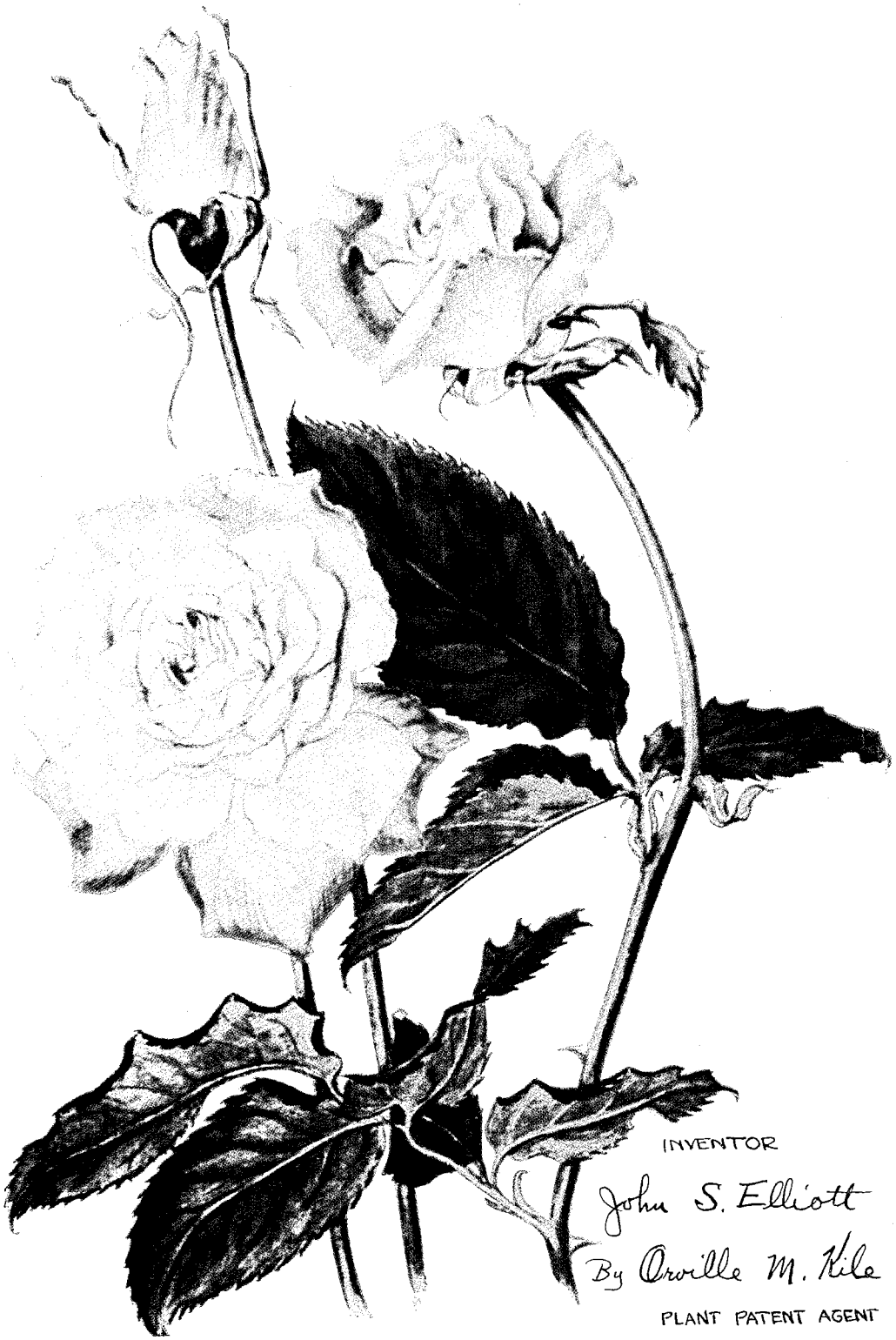
INVENTOR
John S. Elliott
By Orville M. Kile
PLANT PATENT AGENT Patented Mar. 12, 1940

Plant Pat. 370

UNITED STATES PATENT OFFICE

370

ROSE PLANT

John S. Elliott, Dover, N. H.

Application July 11, 1939, Serial No. 283,914

1 Claim. (Cl. 47—61)

My new discovery relates to roses of the hybrid tea class and particularly to the Talisman type of rose. It developed as a sport of Talisman in my greenhouses and displays many of the Talisman qualities. This sport was actually found growing on and from a Talisman rose plant. However, it differs from its parent in several respects, particularly in that its colors are much deeper and more vivid and it has greater petalage, sturdier growth, stronger stems, and buds which are longer and more pointed.

I have asexually propagated this new variety through several generations and its characteristics appear to be firmly fixed.

The original illustrations accompanying this application show three specimens of the blossoms of this variety in different stages of opening, together with some of the foliage and stems.

Following is a detailed description of this new variety in which color citations refer to Ridgway's Color Standards and Nomenclature.

*The plant*

Growth:

Robust and erect.

Stems:

Strong and upright.

*Color.*—Oil green (Plate V).

*Thorns.*—Many; sharp; white; long; narrow base; hooked downward; irregularly spaced. A few very sharp smaller thorns appear on the under side or the rachis and many small white spines occur on the peduncle.

Foliage:

*Leaves.*—Compound, 3 to 5 leaflets; abundant.

Leaflets:

*Size.*—Large; terminal leaflet measures 3½ to 4 inches by 1½ to 2 inches. Lateral leaflets smaller.

*Color.*—Light green, approximately Spinach Green (Plate V) on the upper surface. Under surface is Bice Green (Plate XVII).

*Shape.*—Elliptical with acuminate tip.

*Edge.*—Wavy; sharply serrated.

*Rachis.*—Grooved above; 2 or 3 very sharp thorns on under surface.

*Stipules.*—Wide; with very long sharp points.

*The flower*

Bud:

*Shape.*—Long, pointed.

*Size.*—From 1½ to 2 inches long.

*Color.*—Between Rose Red (Plate XII) and Eugenia Red (Plate XIII).

*Sepals.*—Long and somewhat foliaceous.

*Peduncle.*—Lettuce Green (Plate V). Has many fine, white spines. Is inclined to nod although very strong.

Bloom:

*Size.*—Large; when fully opened attaining a spread of 4½ to 5 inches.

*Form.*—When partially opened it has the characteristic Talisman cup form with squared top. As it opens further the outer row of petals quill into pointed form and petals of the next row or two turn backward at the tips. When fully open the inner petals open wide displaying a large yellow center composed of many stamens and pistils.

Petals:

*Arrangement.*—Imbricated.

*Substance.*—Outer petals very thick and heavy; inner petals not quite so heavy but of considerable substance.

*Shape.*—Outer petals round with point at apex; cupped; edge wavy; inner petals spatulate with irregular tips and wavy edges.

*Color.*—In the opening rose the color of the outer petals is between Rose Red and Rose Color (Plate XII) on the inner surface, the outer surface being between Spinel Red (Plate XIII) and Rose Red (Plate XII) with a large Light Cadmium (Plate V) aiglet which diffuses into the rose shades in the central portion of the petals. The color of the inner petals is between Peach Red and Begonia Rose (Plate I).

As the rose opens the general color effect of the outer petals becomes Rose Color (Plate XII) or at times even somewhat darker. The inner petals lose much of the peach shades and in some specimens become on the inner surface almost entirely rose colored although of a lighter tint than the outer petals. In other specimens more of the peach shades are retained and the central petals of the opened flower have a color between Flesh Color (Plate XIV) and Jasper Pink (Plate XIII).

The under surface of the outer petals of the open flower is approximately Spinel Pink (Plate XXVI). That of the inner petals is much lighter, being approximately Alizarine Pink (Plate XIII).

*Size.*—Outer petals are very large, many measuring 2¼ by 2¼ inches.

*Reproductive organs*

Pistils:

Short; many; uneven; loosely bunched.

*Stigmas.*—Pale Orange Yellow (Plate III).

*Styles.*—White at base; approximately Indian Lake (Plate XXXVI) on upper portion.

Stamens:

Many; encircle pistils.

*Filaments.*—Irregular and uneven, many extending beyond pistils; Carnelian Red (Plate XIV).

*Anthers.*—Large; Light Orange-Yellow (Plate III), edged with light brown which is approximately Sayal Brown (Plate XXIV).

Ovary:

Large; partly protruding from calyx; forms a pithy ring separating pistils from stamens.

Having thus disclosed my discovery, I claim:

A new and useful variety of Hybrid Tea rose plant of the Talisman type with qualities in combination substantially as shown and described, characterized particularly by its robust and erect growth; its smooth, light green foliage; its strong, heavy stems; its long pointed bud; its excellent keeping qualities; and the intense fragrance and distinctive depth of coloring of its large full blooms, petals of which are much lighter on their reverse side.

JOHN S. ELLIOTT.